United States Patent
De Ferra et al.

(10) Patent No.: US 7,501,533 B2
(45) Date of Patent: Mar. 10, 2009

(54) PROCESS FOR PREPARING LYSOPHOSPHATIDYLCHOLINE

(75) Inventors: Lorenzo De Ferra, Patrica (IT); Stefano Servi, Milan (IT); Ezio Fasoli, Milan (IT); Mauro Anibaldi, Patrica (IT); Daniele Scorretti, Patrica (IT)

(73) Assignee: Chem SpA, Cinisello Balsamo (Milan) (IT)

( * ) Notice: Subject to any disclaimer, the term of this patent is extended or adjusted under 35 U.S.C. 154(b) by 145 days.

(21) Appl. No.: 11/244,395

(22) Filed: Dec. 6, 2005

(65) Prior Publication Data
US 2006/0079703 A1   Apr. 13, 2006

(30) Foreign Application Priority Data
Oct. 13, 2004   (IT) .......................... MI2004A1941

(51) Int. Cl.
*C07F 9/02*   (2006.01)
(52) U.S. Cl. ................. 554/82; 554/168; 556/87
(58) Field of Classification Search ................. 554/168, 554/82; 556/87
See application file for complete search history.

(56) References Cited

OTHER PUBLICATIONS

Carmen et al. Enzyme & Microbial Tech., vol. 26, pp. 630-635, 2000.*
Reginato et al., "Organotin-Mediated Monoacylation of Diols with Reveresed Chemoselectivity: A Convenient Synthetic Method", JOC, vol. 55, pp. 5132-5139.*
Reginato et al., "Organotin-Mediated Monoacylation of Diols with Reveresed Chemoselectivity: A Convenient Synthetic Method", JOC, vol. 55, pp. 5132-5139, 1990.*
Virto, Carmen, et al; "Lysophosphatidylcholine synthesis with Candida Antarctica lipase B (Novozym 435)"; *Enzyme and Microbial Technology*; vol. 26, pp. 630-635 (2000) XP-002193135.
Grigoriev, E.V., et al; "Organotin(IV) chloride complexex with phosphocholine and dimyristoyl-L-α-phosphatidylcholine"; *Applied Organometallic Chemistry, Appl. Organometal. Chem.*; vol. 14, pp. 443-448 (2000) XP-009060010.

* cited by examiner

*Primary Examiner*—Deborah D Carr
(74) *Attorney, Agent, or Firm*—Nixon & Vanderhye

(57) ABSTRACT

Process for preparing lysophosphatidylcholine by selective monoacylation of glycerophosphorylcholine (1), in the presence of an acylating agent and of a dialkyltin derivative, according to the following diagram:

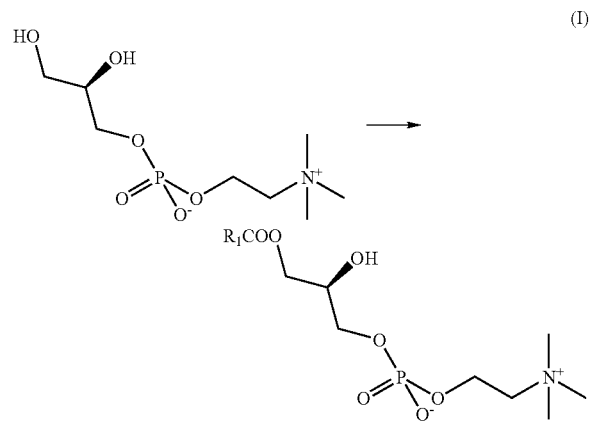

The process is particularly simple and has high overall yields.

44 Claims, 3 Drawing Sheets

Palmitoyl LysoPC (3)

Oleic
Anhydride

POPC (4)

PROCESS FOR PREPARING LYSOPHOSPHATIDYLCHOLINE

The present invention relates to the preparation of lysophosphatidylcholine, and more particularly to the preparation of lysophosphatidylcholine using dialkyltin derivatives.

A lysophospholipid is a glycerophospholipid having a single fatty acid acyl chain bound to the glycerol by an ester bond.

The existence of a polar part and of a lipophile in the molecule imparts particular properties to lysophospholipids and their presence modulates the rigidity and stability of the structures of the cell walls as well as that of artificial model membranes. Lysophospholipids are very widespread in nature, in both animals and plants, although they typically represent only a small fraction of the lipid components of cells.

Some of the most widespread and most thoroughly studied lysophospholipids are the lysophosphatidylcholines (lyso-PCs) whose general formula is shown in FIG. 1 in which $R_1OH$=fatty acid and $R_2$=H or $R_1$=H and $R_2OH$=fatty acid.

In addition to the structural function, lyso-PCs act as regulators of various enzyme activities, and can be used as biological markers to indicate pathological states (see for example JP2002-017398).

The use of lysophospholipids as ingredients in pharmacological formulations is widely documented; for example, lyso-PC has been studied as an ingredient of nasal formulations (Illum et al., Int. J. Pharmaceutic 319 (1992)) and oral formulations (U.S. Pat. No. 4,874,795).

Large quantities of lysophospholipids are also used as emulsifiers in the food industry.

In organic synthesis, they are important intermediates for the preparation of mixed-chain phospholipids (Phospholipids Handbook edited by G. Cevc (1993), pp. 154-155); for example, in the preparation of POPC 4, shown in FIG. 2, lyso-PC is the final intermediate (3) of the synthesis.

In spite of the importance of lyso-PCs in the medical and biological fields and their use in the synthesis of other phospholipids, the preparation procedures are relatively limited.

This is because, although isolation from organic tissues is more useful for analysis than for preparation, the production of lyso-PCs is based primarily on methods described in the literature, which are not absolutely ideal.

These methods are substantially based on two different approaches to synthesis, namely (A) the hydrolysis of a single ester group of phosphatidylcholine or (B) the monoacylation of glycerophosphorylcholine (GC), in purely chemical or chemical/enzymatic experimental conditions and with a greater or lesser degree of selectivity.

The most widely used hydrolytic method (A) exploits the selective hydrolysis of the only ester group linked to position sn-2 of phosphatidylcholine in the presence of phospholipase $A_2$ as shown in FIG. 3.

The reaction is carried out in an aqueous medium in which the subsequent equilibrium between the two forms of lyso-PC derived from the migration of the acyl group is established. The ratio between the two forms is typically 9:1 with the predominance of the form with the acyl group linked to position sn-1 (Dennis et al., Biochemistry 1743(1982)).

However, this reaction, even if carried out on an industrial scale, is not entirely optimal, since it presents the difficult problem of recovering the product from the aqueous reaction mixture from which it can only be extracted or isolated with difficulty, because of its characteristics of solubility and surface-active properties. Another unfavourable aspect is the fact that the principal source of phospholipase $A_2$ is pig pancreas, which may lead to viral contamination which is highly undesirable when the end product is intended for pharmaceutical use.

On the other hand, another enzymatic hydrolytic method for preparing lysophospholipids makes use of the selective hydrolysis of the acyl group linked to position sn-1 of the glycerol of the phospholipids; in this case, however, in order to prepare the lyso-PCs acylated at sn-1 it is necessary to make the acyl substitute migrate subsequently from sn-2 to position sn-1.

Among the selective monoacylation processes described in the literature, we shall mention that disclosed by Paltauf and others in EP 161519, centered on the use of the triphenylmethyl group for the selective protection of the primary alcohol function of the glycerophosphorylcholine (GPC) (I); this method advantageously eliminates the use of phospholipase $A_2$, and of water as the solvent, but on the other hand it is rather laborious, the yield is not always satisfactory, it requires the chromatographic isolation of the intermediate, and, because of the mass of the triphenylmethyl group, generates considerable quantities of by-products.

Selective monoacylation in the presence of immobilized enzymes has been proposed as an alternative for the preparation of some deacylated phospholipids (Adlercreutz et al., Enz. Microb. Technol. 630 (2000)). In this case the selectivity is good, but the low specific activity of the enzyme makes it necessary to use such large quantities of it as to make this method unsuitable for industrial application.

We have now discovered that it is possible to overcome the disadvantages associated with the methods of preparation described above, and to synthesize lyso-PCs advantageously on a large scale with a single chemical process, with generally high yields, using inexpensive reagents which are readily available on the market, and avoiding the use of water as a solvent, with consequent simplification of the final isolation procedure.

BRIEF DESCRIPTION OF THE INVENTION

The process to which the present invention relates comprises selective monoacylation at position sn-i of GPC (I), a commercially available substance, with an acylating agent in the presence of dialkyltin derivatives according to the diagram in FIG. 4.

DETAILED DESCRIPTION OF THE INVENTION

The process proposed by the present invention comprises the selective monoacylation of GPC (I) in the presence of dialkyltin derivatives.

The use of dialkyl derivatives of tin in diol acylation reactions has been reported in the literature (see for example Hanessian, Tetrahedron 643 (1985)) and is applied mainly to the selective protection of carbohydrates.

Figure 1:
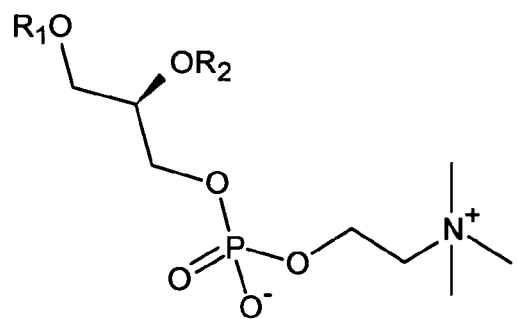
FIG. 1 is a general formula of lysophosphatidylcholines.
Figure 2:
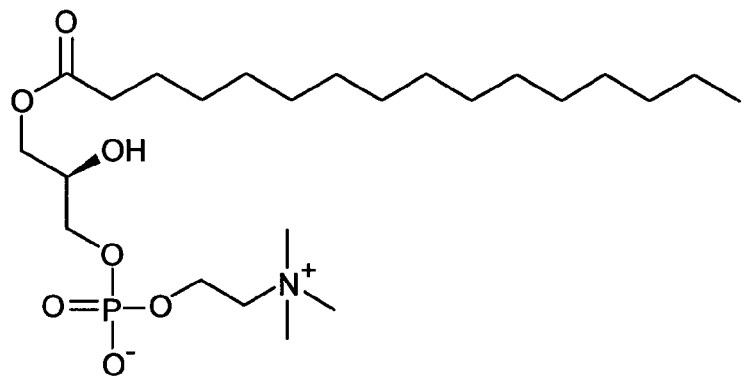
FIG. 2 is POPC (4) and palmitoyl lysoPC (3)
Figure 2:
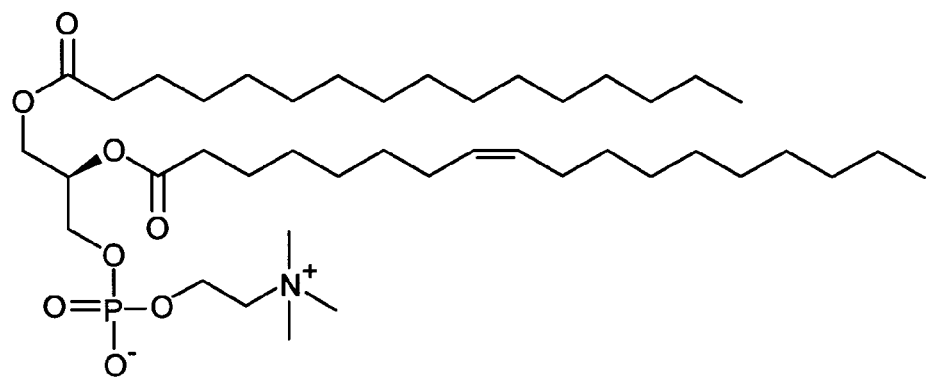
Figure 3:
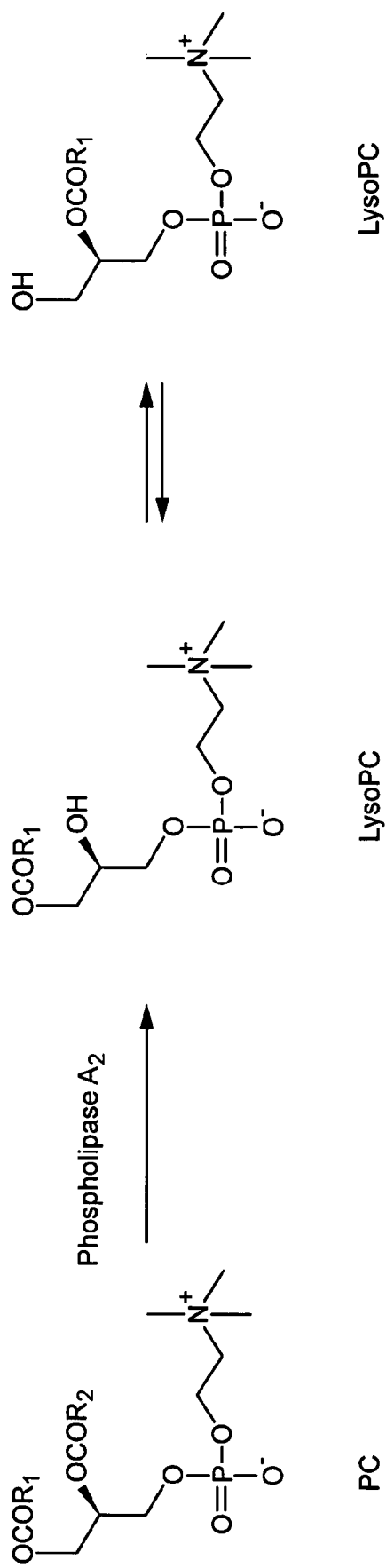
FIG. 3 is the selective hydrolysis of phosphatidylcholine in the presence of phospholipase $A_2$.
Figure 4:
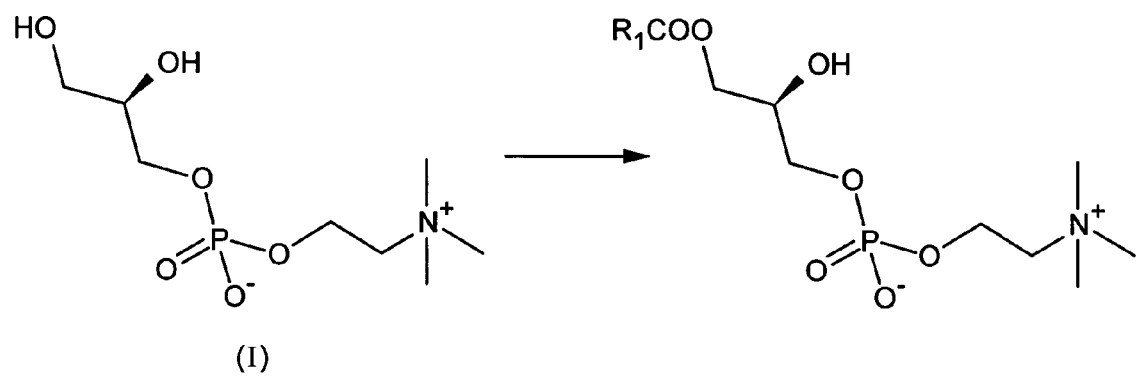
FIG. 4 is the selective monoacylation of GPC (I) with an acylation agent in the presence of dialkyltin derivatives.
Figure 5:
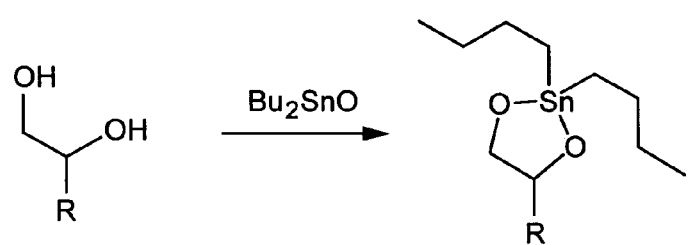
FIG. 5 is the formation of a stannylene using dibutyltin oxide.

The tin compound is considered to have the function of selectively activating one of the oxygen atoms of the substrate by forming a stannylene of the type shown in FIG. 5.

The most commonly used reagent is dibutyltin oxide, but dimethyltin oxide and dimethyltin dimethoxide have recently been proposed as more reactive substitutes. The reaction solvent most commonly used in the prior art for the formation of stannylene is toluene. A procedure based on the use of microwaves to enable dibutyltin oxide to be used in catalytic quantities has also been described (Herradon and others, Synlett 455 (1995)).

GPC (I) has a very low solubility in apolar organic solvents, such as toluene, commonly used in reactions of acylation in the presence of tin derivatives; furthermore, the phosphate group present in its structure interacts strongly with dialkyltin compounds (see Appl. Organometal. Chem. 443 (2000)), altering their reactivity. In view of these characteristics, it would perhaps be logical to conclude that GPC (I) is not a suitable substrate for this kind of acylation.

Surprisingly, however, we have found that, in spite of these unfavourable presumptions, it is possible to carry out the aforesaid monoacylation reaction with high yields, and also that this can be done even with catalytic quantities of tin compound, without the need to use microwave equipment or the dimethyltin derivatives which have undesirable toxicity characteristics.

Anhydrides or chlorides of fatty acids, preferably chlorides, can be used as acylating agents in the reaction; the fatty acids can be saturated, unsaturated or polyunsaturated, with chains varying in length from 6 to 30 carbon atoms. The said acylating agent is generally used in quantities in the range from 100% to 200%, and preferably from 100% to 120%, in terms of moles per mole of glycerophosphorylcholine.

These compounds are generally commercially available or can be prepared by known procedures.

The tin derivative to be used in this process has a structure in which two alkyl groups are bonded to the tin atom; these groups can be identical to or different from each other, can contain 1 to 18 carbon atoms or can be polymeric in nature. In the last-mentioned case, the tin derivative can be removed at the end of the reaction by simple filtration, and the reagent can be recycled in the next reaction. The tin atom is also bonded to two halogens (for example dialkyltin dichlorides) or two alkoxy groups (dialkyltin dialkoxides) or acyloxy groups (for example dialkyltin diacetates), or to an oxygen atom with a double bond (diallcyltin oxides, for example dibutyltin oxide).

According to the present invention, the preferred tin derivatives are dialkyltin oxides, of which dibutyltin oxide and dioctyltin oxide are most preferable.

These compounds are generally commercially available or can be prepared by known procedures.

Tin derivatives with long alkyl chains, particularly octyl derivatives, are particularly preferable in the present procedure, since they are less toxic, as indicated by the following values of acute oral toxicity in rats (Sax and others, Dangerous Properties of Industrial Materials, edition VII).

| dibutyltin oxide | LD50 = 44.9 mg/kg |
| dioctyltin oxide | LD50 = 2500 mg/kg |

The tin derivative is used in a quantity ranging from 0.1 to 110 mol % with respect to the substrate, preferably from 5 to 100%, and more preferably from 20 to 100%.

In order to be able to use the dialkyltin derivative in catalytic quantities, it is generally sufficient to increase the quantity of acylating agent until the reaction is completed. Normally, with a stoichiometric ratio, in moles, of dialkyltin to substrate of 0.2:1,an excess of acylating agent of approximately 50% is sufficient. In the monoacylation process proposed by the present invention it is advantageous to use a base, preferably an amine base, to control the increase in acidity in the medium in the course of the reaction.

The quantity of the base during acylation can range from 30 to 140 mol % with respect to the substrate, and preferably from 100 to 120%.

Various amines, such as triethylamine or 4-diinethylaminopyridine (DMAP), which may affect the selectivity of the reaction, can be used as the base.

In particular, if triethylamine is used, the ratio between the acylation product in positions sn-1 and sn-2 of the glycerol has been found to be 9:1,and thus equal to that obtained by the equilibration reaction in water of the monoacyl derivative and also, as mentioned above, in the hydrolytic process with phospholipase $A_2$.

The product obtained with this new process can therefore directly replace that obtained by the conventional procedures as regards the composition of the final mixture.

In another embodiment of the present invention, a further improvement of selectivity was achieved by using 4-dimethylaminopyridine (DMAIP) as the base. In this case, the acylation ratio between the positions sn-1 and sn-2 in the final lyso-PC was found to be approximately 50:1.

According to the present invention, the preferred bases are amines, more preferably tertiary amines, and even more preferably triethylamine and DMAP. The reaction temperature can vary from 0° C. to the boiling point of the solvent used. Preferably, the temperature is in the range from 40° to the reflux temperature of the solvent in the stannylene formation stage, while it is in the range from 10 to 40° C. in the acylation stage.

The process can be carried out in various organic solvents such as alcohols, ethers, esters, aromatic or aliphatic hydrocarbons or chlorinated solvents.

The preferred solvents are alcohols, such as secondary alcohols, particularly isopropanol.

In a preferred embodiment of the present invention, we have found that isopropanol can be used advantageously as a solvent for the whole process, in other words both in the preliminary formation of the stannylene and in the subsequent stage of acylation, with a considerable simplification of the experimental procedure by comparison with what has been described in the prior art for similar reactions.

This is because, in the monoacylation of 1,2-diols with the aid of dibutyltin oxide, there is normally preliminary formation of stannylene in an aromatic solvent, such as toluene, by azeotropic removal of water, and it is only after this lengthy stage of the process that the acylation proper is continued in another solvent such as chloroform (see for example Roelens and others, JOC 5 132(1990))

There are also reports in the literature (Moffat and others, (JOG 24(1974)) concerning the monoacylation of nucleosides, using dibutyltin oxide in an alcohol solvent (methanol), but this transformation requires the use of an excess of acyl chloride ranging from 400 mol % to 900 mol % with respect to the substrate.

Surprisingly, however, we have found that, for the completion of the reaction of monoacylation of GPC (I), all that is required is a modest molar excess of acylating agent, normally approximately 20% when the solvent if isopropanol, the concomitant reaction between the acylating agent and the alcohol solvent being fairly limited.

In a variant of the present process, it is also possible to use a combined method, in which the stannylene is prepared in methanol, the reaction solvent is replaced with isopropanol, and the process is continued with the acylation in the latter solvent.

In a particularly preferred embodiment of the present invention, the GPC is made to react in methanol with 1 equivalent of dibutyltin oxide in methanol, and 1.2 equivalents of triethylamine and 1.2 equivalents of a fatty acid chloride are added after the methanol has been replaced with isopropanol.

The transformation yields of the present process are generally high, typically in the range from 80 to 100 mol % the reagents used are inexpensive and readily available on the market, and if necessary the fatty acid chlorides or the corresponding anhydrides can be prepared by the conventional methods reported in the literature. For these reasons, this procedure can conveniently be used to produce lyso-PCs on a large scale.

A further advantage of this process consists in the fact that the reaction is carried out without the use of water as a solvent, and this, as is known to those skilled in the art, enables the isolation of the lyso-PCs to be greatly simplified.

Conventional isolation techniques such as crystallization or chromatographic separation can be used. A particularly favourable aspect is the possibility of isolating the product with a high yield and high purity by crystallization, by adding a suitable organic solvent to the reaction mixture and cooling it.

In order to illustrate the present invention more clearly, the following examples will now be provided, these examples representing only some of the possible embodiments of the invention and not being intended to limit its scope in any way.

EXAMPLES

Abbreviations
GPC=sn-glycero-3-phosphocholine (I)
DBTO=dibutyltin oxide
DOTO=dioctyltin oxide
TEA=triethylamine
DMAP=dimethylamine pyridine
IIPA=isopropanol Example 1

Palmitoyl-lyso-PC

A suspension of 2.5 g of GPC (I) (1 eq.), 2.5 g of DBTO (1 eq) and 35 ml of methanol was stirred at reflux to form a clear solution (1.5 hrs.) and the methanol was evaporated to leave a residue of 5 ml. 25 ml of WA was added, the mixture was concentrated again at ordinary pressure to give a residual volume of 5 ml, and 25 ml of IPA was added. 1.6 ml of TEA (1.2 eq) and 3.2 g of palmitoyl chloride (1.2 eq) were dropped in at 25° C. At the end of the dropping, the conversion ($^{31}$P-NMR) was >99%, and the ratio between the two lyso-PCs was 1:9 in favour of the compound acylated at position sn-1.

Example 2

Stearoyl-lyso-PC

A suspension of 0.5 g of GPC, 0.5 g of DBTO (1 eq), and 10 ml of methanol was stirred at reflux until a clear solution was obtained (1 hr); the solvent was evaporated from the solution to give a residual volume of 1.ml. 5 ml of IPA was added, the mixture was concentrated again at ordinary pressure to give a residual volume of 1 ml, and 5 ml of IPA was added. 0.324 ml of TEA (1.2 eq) and 0.62 g of palmitoyl chloride (1.2 eq) were dropped in at 25° C. At the end of the dropping, the conversion ($^{31}$P-NMR) was 92%, and the ratio between the two forms of lyso-PC was 1:9 in favour of the compound acylated at position sn-1.

Example 3

Oleoyl-lyso-PC

A suspension of 10 g of GPC (I) and 10.65 g of DBTO in 350 ml of IPA was heated at reflux for 1 hr. 5.96 ml of TEA and 12.9 g of oleoyl chloride were dropped on to the resulting suspension after it had been cooled to 0° C. The solution was stirred for 15 mins. at ambient temperature and a specimen of the mixture was analysed by HPLC; the ratio of oleoyl lyso-PC to GPC was 97:3 (100 diol Lichrospher column, ELS detector).

Example 4

Palmitoyl-lyso-PC

A suspension of 2.5 g of GPC (I) (1 eq.), 0.5 g of DBTO (0.2 eq), and 35 ml of methanol was stirred at reflux for 1 hr, to produce a clear solution from which the methanol was evaporated to give a residual volume of 5 ml. 25 ml of IPA was added and the solution was evaporated to a volume of 5 ml, another 25 ml of IPA being added to the residue. 1.6 ml of TEA (1.2 eq) was dropped in, the temperature was raised to 40° C., and 3.2 g (1.2 eq) of palmitoyl chloride was dropped in, the reaction being sampled at the end of the dropping.

Another 0.8 eq. of TEA was added and 0.8 eq. of palmitoyl chloride was dropped in. The conversions ($^{31}$PNMR) were 90% after the first step and >99% after the second step of dropping (2 eq. total).

25 ml of heptane was added to the solution, which was then cooled to 0° C. and filtered. This produced 7.6 g of wet product which was recrystallized by a mixture of heptanol and IPA, resulting in 4.4 g of lyso-PC after drying (a yield of 92%).

Example 5

Palmitoyl-lyso-PC 2.5 g of GPC (I), 3.5 g of DOTO (1 eq), and 35 ml of methanol were placed in a three-necked flask under a nitrogen flow, and were stirred at reflux temperature for two hours; the result was a white suspension to which 24 ml of IPA was added and then evaporated at ordinary pressure. IPA (50 ml) was added to the residue and the suspension was left to cool to 25° C. When the temperature was stabilized, 1.62 ml of TEA (1.2 eq) and 3.24 g of palmitoyl chloride (1.2 eq) were dropped in. The conversion ($^{31}$PNMR) was >99%, and the ratio between the two lyso-PCs was 1:9 in favour of the compound acylated at position sn-1.

Example 6

Palmitoyl-lyso-PC

A suspension of 2.5 g of GPC (I) and 2.5 g of DBTO in 125 ml of IPA was stirred at reflux temperature for 1 hr. After the temperature had been raised to 40° C., 1.62 ml of TEA and 3.24 g of palmitoyl chloride were dropped in. The conversion to palmitoyl-lyso-PC was 88% ($^{31}$P NMR).

Example 7

Palmitoyl-lyso-PC

A suspension of 0.5 g GPC (I), 0.5 g DBTO (1 eq), and 10 ml methanol was stirred at reflux until a clear solution was obtained (1 hr.) and the methanol was evaporated to a residual volume of 1 ml. 5 ml of IPA was added and the solution was concentrated again at ordinary pressure to a residual volume of 1 ml, after which 5 ml of WA was added. At 25° C., 0.220 g of DMAP (1.2 eq) was added and 0.64 g of palmitoyl chloride (1.2 eq) was dropped in. At the end of the dropping, the conversion ($^{31}$PNMR) was 86%, and the ratio between the two forms of lyso-PC was 1:50 in favour of the compound acylated at position sn-1.

Example 8

Palmitoyl-lyso-PC

A suspension of 2.5 g GPC (I), 2.5 g DBTO (1 eq), and 35 ml methanol was stirred at reflux until a clear solution was obtained (1.5 hr.), after which the methanol was evaporated to a residue of 5 ml. 25 ml of WA was added, the mixture was concentrated again at ordinary pressure to a residual volume of 5 ml, and 25 ml of WA was added. 1.6 ml TEA (1.2 eq) and 3.2 g palmitoyl chloride (1.2 eq) were added by dropping at 25° C. The conversion ($^{31}$PNIvIR) at the end of the dropping was >98%. 25 ml of heptane was added to the suspension and, after cooling to 0° C. and holding at 0° C. for 30 minutes, 5.2 g of solid was obtained by filtration. The solid was recrystallized in heptanol/WA, giving 4.7 g of high-purity product after drying (a yield of 98%).

The invention claimed is:

1. A process for preparing lysophosphatidylcholine, comprising selectively monoacylating glycerophosphorylcholine at position sn-1 with an acylating agent in the presence of a dialkyltin derivative in which said dialkyltin derivative has two alkyl groups bound to the tin atom, said groups being identical to or different from each other, containing from 1 to 18 carbon atoms or polymeric in nature, and two halogens or two alkoxy or acyloxy groups or an oxygen atom bound by a double bond.

2. The process according to claim 1, in which said acylating agent is an anhydride or chloride of a fatty acid.

3. The process according to claim 1, in which said acylating agent is used in a quantity, in moles, ranging from 100 to 200% per mole of glycerophosphorylcholine.

4. The process according to claim 1, in which said dialkyltin derivative is a dialkyltin oxide.

5. The process according to claim 1, in which said dialkyltin derivative is used in quantities ranging from 0.1 to 110% mol % with respect to the glycerophosphorylcholine.

6. The process according to claim 1, in which said dialkyltin derivative is used in catalytic quantities with respect to the glycerophosphorylcholine.

7. The process according to claim 1, in which said monoacylation reaction is carried out in the presence of a base.

8. The process according to claim 7, in which said base is used in a molar ratio ranging from 30 to 140% with respect to the glycerophosphorylcholine.

9. The process according to claim 1, in which the process is carried out in the presence of an organic solvent and a stannylene is formed.

10. The process according to claim 1, in which the reaction solvent is selected from the group consisting of alcohols, ethers, esters, aromatic hydrocarbons, aliphatic hydrocarbons and chlorinated solvents.

11. The process according to claim 9, in which the reaction solvent is methanol in the stage of formation of the stannylene and isopropanol in the acylation stage.

12. The process according to claim 9, in which the solvent is isopropanol both in the stage of formation of the stannylene and in the acylation stage.

13. The process according to claim 1, in which the solvent is isopropanol and said acylating agent is used in a molar excess of approximately 20% with respect to the glycerophosphorylcholine.

14. The process according to claim 1, in which the glycerophosphorylcholine is made to react in methanol with 1 equivalent of dibutyltin oxide in methanol, and 1.2 equivalents of triethylamine and 1.2 equivalents of a fatty acid chloride are added after the methanol has been replaced with isopropanol.

15. The process according to claim 9, in which the temperature of the reaction is in the range from 40° C to the reflux temperature of the solvent in the stage of formation of the stannylene and from 10 to 40° C in the acylation stage.

16. The process according to claim 2, in which said acylating agent is a chloride of a fatty acid.

17. The process according to claim 3, in which said acylating agent is used in a quantity, in moles, ranging from 100 to 120% per mole of glycerophosphorylcholine.

18. The process according to claim 4, in which said dialkyitin derivative is dibutyltin oxide or dioctyltin oxide.

19. The process according to claim 5, in which said dialkyltin derivative is used in quantities ranging from 5 to 100% mol % with respect to the glycerophosphorylcholine.

20. The process according to claim 5, in which said dialkyltin derivative is used in quantities ranging from 20 to 100% mol % with respect to the glycerophosphorylcholine.

21. The process according to claim 7, in which said monoacylation reaction is carried out in the presence of a tertiary amine.

22. The process according to claim 7, in which said monoacylation reaction is carried out in the presence of triethylamine or 4-dimethylaminopyridine (DMAP).

23. A process for preparing lysophosphatidylcholine, comprising selectively monoacylating glycerophosphorylcholine at position sn-1 with an acylating agent in the presence of a dialkyltin derivative and in the absence of water, in which said dialkyltin derivative has two alkyl groups bound to the tin atom, said groups being identical to or different from each other, containing from 1 to 18 carbon atoms or polymeric in nature, and two halogens or two alkoxy or acyloxy groups or an oxygen atom bound by a double bond.

24. The process according to claim 23, in which said acylating agent is an anhydride or chloride of a fatty acid.

25. The process according to claim 23, in which said acylating agent is used in a quantity, in moles, ranging from 100 to 200% per mole of glycerophosphorylcholine.

26. The process according to claim 23, in which said dialkyltin derivative is a dialkyltin oxide.

27. The process according to claim 23, in which said dialkyltin derivative is used in quantities ranging from 0.1 to 110% mol % with respect to the glycerophosphorylcholine.

28. The process according to claim 23, in which said dialkyltin derivative is used in catalytic quantities with respect to the glycerophosphorylcholine.

29. The process according to claim 23, in which said monoacylation reaction is carried out in the presence of a base.

30. The process according to claim 29, in which said base is used in a molar ratio ranging from 30 to 140% with respect to the glycerophosphorylcholine.

31. The process according to claim 23, in which the process is carried out in the presence of an organic solvent and a stannylene is formed.

32. The process according to claim 31, in which the temperature of the reaction is in the range from 40° C to the reflux temperature of the solvent in the stage of formation of the stannylene and from 10 to 40° C in the acylation stage.

33. The process according to claim 23, in which the reaction solvent is selected from the group consisting of alcohols, ethers, esters, aromatic hydrocarbons, aliphatic hydrocarbons and chlorinated solvents.

34. The process according to claim 31, in which the reaction solvent is methanol in the stage of formation of the stannylene and isopropanol in the acylation stage.

35. The process according to claim 31, in which the solvent is isopropanol both in the stags of formation of the stannylene and in the acylation stage.

36. The promo according to claim 23, in which the solvent is isopropanol and said acylating agent is used in a molar excess of approximately 20% with respect to the glycerophosphorylcholine.

37. The process according to claim 23, in which the glycerophosphorylcholine is made to react in methanol with 1 equivalent of dibutyltin oxide in methanol, and 1.2 equivalents of triethylamine and 1.2 equivalents of a fatty acid chloride are added after the methanol has been replaced with isopropanol.

38. The process according to claim 24, in which said acylating agent is a chloride of a fatty acid.

39. The process according to claim 25, in which said acylating agent is used in a quantity, in moles, ranging from 100 to 120% per mole of glycerophosphorylcholine.

40. The process according to claim 27, in which said dialkyltin derivative is dibutyltin oxide or dioctyltin oxide.

41. The process according to claim 28, in which said dialkyltin derivative is used in quantities ranging from 5 to 100% mol % with respect to the glycerophosphorylcholine.

42. The process according to claim 28, in which said dialkyltin derivative is used in quantities ranging from 20 to 100% mol % with respect to the glycerophosphorylcholine.

43. The process according to claim 30, in which said monoacylation reaction is carried out in the presence of a tertiary amine.

44. The process according to claim 30, in which said monoacylation reaction is carried out in the presence of triethylamine or 4-dimethylaminopyridine (DMAP).

* * * * *